(12) United States Patent
Gollier et al.

(10) Patent No.: US 7,979,241 B2
(45) Date of Patent: Jul. 12, 2011

(54) OPTIMIZED METHOD FOR LID BIOSENSOR RESONANCE DETECTION

(75) Inventors: Jacques Gollier, Painted Post, NY (US); Garrett A. Piech, Horseheads, NY (US); Michael B. Webb, Lindley, NY (US); Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 286 days.

(21) Appl. No.: 12/266,060

(22) Filed: Nov. 6, 2008

(65) Prior Publication Data

US 2009/0138205 A1 May 28, 2009

Related U.S. Application Data

(63) Continuation of application No. 11/716,425, filed on Mar. 9, 2007, now Pat. No. 7,509,239.

(60) Provisional application No. 60/781,397, filed on Mar. 10, 2006.

(51) Int. Cl.
*H03F 1/26* (2006.01)
(52) U.S. Cl. ............ 702/191
(58) Field of Classification Search .......... 702/191; 435/6; 356/369, 445; 73/602
See application file for complete search history.

(56) References Cited

U.S. PATENT DOCUMENTS

| | | | | |
|---|---|---|---|---|
| 4,545,250 A * | 10/1985 | Miwa | | 73/602 |
| 4,815,843 A | 3/1989 | Tiefenthaler et al. | | 356/128 |
| 6,100,975 A * | 8/2000 | Smith et al. | | 356/301 |
| 6,677,873 B2 | 1/2004 | Berezin | | 341/131 |
| 7,239,395 B2 | 7/2007 | Gollier | | 356/445 |
| 2003/0059820 A1 * | 3/2003 | Vo-Dinh | | 435/6 |
| 2005/0044519 A1 | 2/2005 | Sengupta et al. | | 716/11 |
| 2005/0264818 A1 | 12/2005 | Gollier | | 356/445 |
| 2006/0017923 A1 | 1/2006 | Ruchti et al. | | 356/326 |
| 2006/0141611 A1 | 6/2006 | Frutos et al. | | 435/287.2 |
| 2006/0180750 A1 | 8/2006 | Gollier et al. | | 250/227.11 |

FOREIGN PATENT DOCUMENTS

| | | |
|---|---|---|
| EP | 1 236 807 | 9/2002 |
| WO | WO 2004/083820 | 9/2004 |

OTHER PUBLICATIONS

K. Tiefenthaler et al., "Integrated Optical Switches and Gas Sensors", Apr. 1984, Optics Letters, vol. 10, No. 4, pp. 137-139.
K. Cattier et al., "Label-free highly sensitive detection of (small) molecules by wavelength interrogation of integrated optical chips", Sensors and Actuators B, 2003, vol. 91, pp. 241-251.
M. Wiki et al., "Novel integrated optical sensor based on a grating coupler triplet", Biosensor & Bioelectronics, vol. 13, 1998, pp. 1181-1185.

* cited by examiner

*Primary Examiner* — Drew A Dunn
*Assistant Examiner* — Xiuquin Sun
(74) *Attorney, Agent, or Firm* — Gregory B. Butler; Thomas R. Beall

(57) ABSTRACT

An optical interrogation system is described herein that can interrogate a label-independent-detection (LID) biosensor and monitor a biological event on top of the biosensor without suffering from problematical parasitic reflections and/or problematical pixelation effects. In one embodiment, the optical interrogation system is capable of interrogating a biosensor and using a low pass filter algorithm to digitally remove problematical parasitic reflections contained in the spectrum of an optical resonance which makes it easier to determine whether or not a biological event occurred on the biosensor. In another embodiment, the optical interrogation system is capable of interrogating a biosensor and using an oversampling/smoothing algorithm to reduce oscillations in the estimated location of an optical resonance caused by the problematical pixelation effect which makes it easier to determine whether or not a biological event occurred on the biosensor.

22 Claims, 13 Drawing Sheets

US 7,979,241 B2

OPTIMIZED METHOD FOR LID BIOSENSOR RESONANCE DETECTION

CROSS-REFERENCE TO RELATED APPLICATIONS

This application is a continuation application of U.S. patent application Ser. No. 11/716,425, filed Mar. 9, 2007, now U.S. Pat. No. 7,509,239, which claims the benefit of U.S. Provisional Patent Application Ser. No. 60/781,397 filed Mar. 10, 2006. The contents of these documents are hereby incorporated by reference herein.

BACKGROUND OF THE INVENTION

1. Field of the Invention

The present invention relates to an optical interrogation system that can interrogate a label-independent-detection (LID) biosensor and monitor a biological event on top of the biosensor without suffering from problematical parasitic reflections and/or problematical pixelation effects.

2. Description of Related Art

Today non-contact optical sensor technology is used in many areas of biological research to help perform increasingly sensitive and time-constrained assays. In these assays, an optical interrogation system is used to monitor changes in the refractive index or variations in the optical response/optical resonance of an optical biosensor as a biological substance is brought into a sensing region of the biosensor. The presence of the biological substance alters the optical resonance of the biosensor when it causes a bio-chemical interaction like material binding, adsorption etc. . . . It is this alteration of the optical resonance that enables one to use the biosensor to directly monitor biological events in label-free assays where the expense and experimental perturbations of fluorescent dyes are completely avoided.

The optical interrogation system needs to implement some sort of resonance detection algorithm to determine whether or not a biological event (e.g., binding of a drug to a protein) occurred on the biosensor. To ensure that one can detect a small biochemical binding event, the resonance detection algorithm needs to be designed to sense small shifts in the resonance spectral location or the resonance angular location, wherein the shifts are often a very small fraction of the resonance width itself. For example, a typical resonance width for a resonant waveguide grating biosensor may be ~1 nm, but a small biochemical binding event might present a change of only ~0.001 nm. Unfortunately, today it is difficult to properly optimize the resonance detection algorithm because both the resolution and linearity of the optical resonance of a biosensor 102 may be adversely affected by: (1) the presence of measurement noise caused by problematical parasitic reflections; and/or (2) the presence of measurement artifacts caused by problematical pixelation effects. Thus, there is a need for an optical interrogation system that can optimize the detection of the optical resonance by addressing the problematical parasitic reflections and/or problematical pixelation effects. This need and other needs are satisfied by the optical interrogation system and method of the present invention.

BRIEF DESCRIPTION OF THE INVENTION

The present invention includes an optical interrogation system that can interrogate a label-independent-detection (LID) biosensor and monitor a biological event on top of the biosensor without suffering from problematical parasitic reflections and/or problematical pixelation effects. In one embodiment, the optical interrogation system is capable of interrogating a biosensor and using a low pass filter algorithm to digitally remove problematic parasitic reflections contained in the spectrum of an optical resonance which makes it easier to determine whether or not a biological event occurred on the biosensor. In another embodiment, the optical interrogation system is capable of interrogating a biosensor and using an oversampling/smoothing algorithm to reduce oscillations in the estimated location of an optical resonance caused by the problematical pixelation effect which makes it easier to determine whether or not a biological event occurred on the biosensor.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
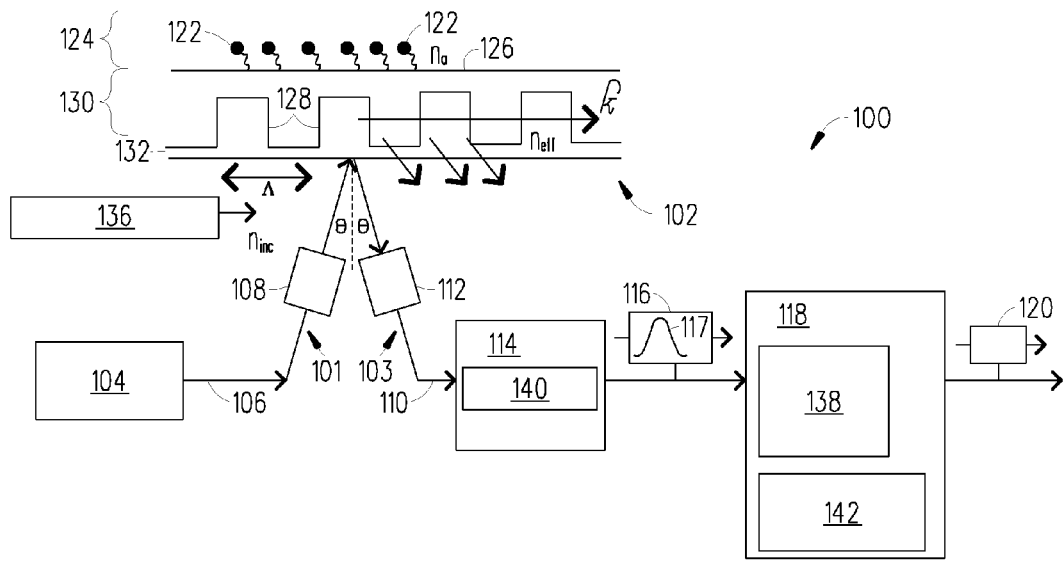
FIG. 1 is a block diagram of an optical interrogation system configured to function in accordance with two different embodiments of the present invention.

Referring to FIG. 1, there is a block diagram of an optical interrogation system 100 that can interrogate a biosensor 102 in accordance with the present invention. As shown, the optical interrogation system 100 has a launch system 101 which includes a light source 104 (e.g., broad spectrum light source 104) that outputs an optical beam 106 (e.g., white light beam 106) into a lensed fiber optic 108 which emits the optical beam 106 towards the biosensor 102 (e.g., grating coupled waveguide biosensor 102). The optical interrogation system also includes a receive system 103 which has a lensed fiber optic 112 that receives an optical beam 110 reflected from the biosensor 102. Alternatively, the launch optic 108 and receive optic 112 can be a single optic, an exemplary single fiber interrogation system is disclosed in co-assigned U.S. patent application Ser. No. 11/058,155 filed on Feb. 14, 2005. The contents of this document are incorporated by reference herein. The receive system 103 also includes a detector 114 (e.g., spectrometer 114, CCD array 140) which receives the reflected optical beam 110 from the lensed fiber optic 112. The detector 114 outputs a signal 116 (which is representative of the spectral resonance 117) to a processor 118. The processor 118 processes the signal 116 and optimizes the detection of the position of the spectral resonance 117 by addressing the problematical parasitic reflections and/or the problematical pixelation effects. Then, the processor 118 outputs an optimized signal 120 which is used to monitor a biological event (e.g., biological binding of ligand to analyte) on top of the biosensor 102. How the processor 118 optimizes the signal 116 is described in detail after a brief description is provided about the structure and operation of the biosensor 102.

The biosensor 102 makes use of changes in the refractive index at its top surface that affect the waveguide coupling properties of the emitted optical beam 106 and the reflected optical beam 110. These changes enable the label-free monitoring of a biological event such as whether or not a biological substance 122 (e.g., cell, molecule, protein, drug, chemical compound, nucleic acid, peptide, carbohydrate) happens to be located on the biosensor's superstrate 124 (sensing region 124). For instance, the biological substance 122 is typically located within a bulk fluid which is deposited on the biosensor's superstrate 124. And, it is the presence of this biological substance 122 in the bulk fluid that alters the index of refraction at the biosensor's top surface 126.

The biosensor's 102 functionality may be best understood by analyzing the structure of its diffraction grating 128 and waveguide 130. The optical beam 106 that is directed at the diffraction grating 128 can only be coupled into the waveguide 130 if its wave vector satisfies the following resonant condition as shown in equation no. 1:

$$k_x' = k_x - \kappa \quad [1]$$

where $k_x'$ is the x-component of the incident wave vector, $K_x$ is the guided mode wave vector, and $\kappa$ is the grating vector. The grating vector $\kappa$ is defined as a vector having a direction perpendicular to the lines of the diffraction grating 128 and a magnitude given by $2\pi/\Lambda$ where $\Lambda$ is the grating period (pitch). This expression may also be written in terms of wavelength $\lambda$ and incident angle $\theta$ as shown in equation no. 2:

$$\frac{2\pi n_{inc}}{\lambda} \sin\theta = \frac{2\pi n_{eff}}{\lambda} - \frac{2\pi}{\Lambda} \quad [2]$$

where $\theta$ is the angle of incidence of the optical beam 106, $n_{inc}$ is the index of refraction of the incident medium, $\lambda$ is the wavelength of the optical beam 106, and $n_{eff}$ is the effective index of refraction of the waveguide 130. The waveguide 130 has an effective index of refraction that is a weighted average of the indices of refraction that the optical waveguide mode field "sees" as it propagates through the waveguide 130. The optical waveguide mode preferably has a spatial extent that is much wider than the waveguide 130, where the spatial extent depends on the refractive index of the substrate 132. As a result, the optical waveguide mode has an evanescent wave/tail that extends into the superstrate 124 (sensing region 124) which "sees" any surface changes created when the biological substance 122 approaches or comes in contact with the biosensor's top surface 126.

Figure 2:
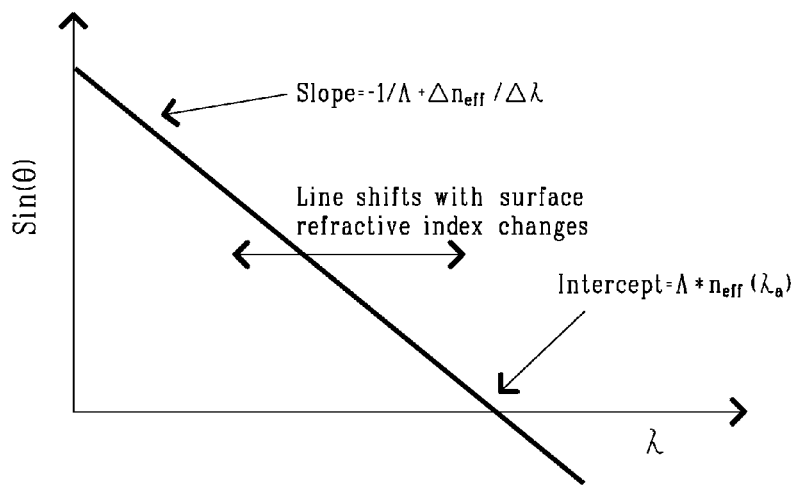
FIGS. 2-10 are drawings and graphs used to help describe how the optical interrogation system can function to reduce measurement noise caused by problematical parasitic reflections in accordance with the first embodiment of the present invention.

The previous expression shown in equation no. 2 may be rewritten in the more convenient form shown in equation no. 3:

$$\sin\theta = n_{eff} - \frac{\lambda}{\Lambda} \quad [3]$$

which is the equation of a line where sin θ being the y axis, λ being the x-axis, $\Lambda n_{eff}$ the x-intercept, and $-1/\Lambda$ the slope. To obtain equation no. 3, $n_{inc}$ is set to 1 so that it could be removed from this expression. This approximation is used since air (n~1.0003) is the most common incident medium. This relation is pictured in the graph shown in FIG. 2. When a biological substance 122 binds to the surface 126, then the effective index of the waveguide 122 is altered which leads to the shifting the resonant wavelength or resonant angle of the biosensor 102. This shifting can be seen as a shift of the x-intercept in the line shown in FIG. 2.

Figure 3:
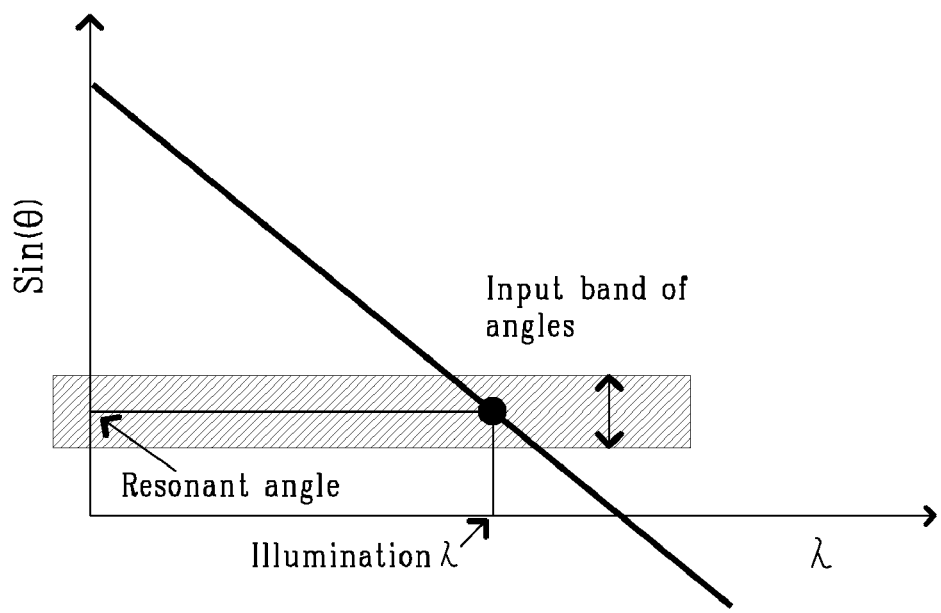
Figure 4:
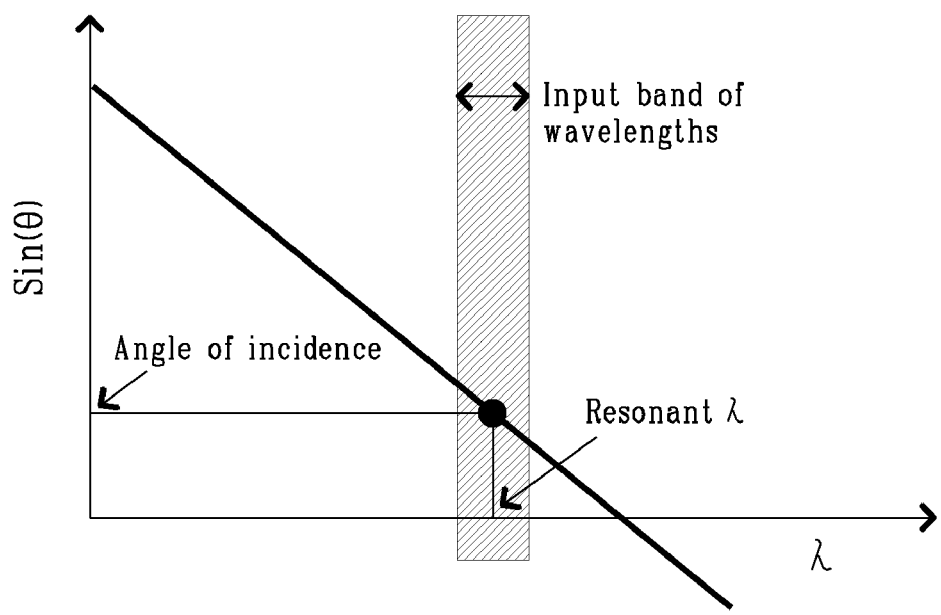

The resonant condition (e.g., resonant wavelength or resonant angle) of such a biosensor 102 may be interrogated to determine refractive index changes by observing the optical beam 110 reflected from the biosensor 102. There are two different modes of operation for monitoring refractive index changes from such a resonant waveguide grating biosensor 102—angular interrogation or spectral interrogation. In angular interrogation, a nominally single wavelength optical beam 106 is focused to create a range of illumination angles and directed into the biosensor 102. The reflected optical beam 110 is received by the detector 114 (e.g., CCD array 114). And, by monitoring the position of the resonant angle reflected by the biosensor 102, one can monitor binding or refractive index changes on or near the biosensor's surface 126. The angular interrogation concept is graphically represented in the graph shown in FIG. 3. In spectral interrogation, a nominally collimated, broadband optical beam 106 is sent into the biosensor 102 and the reflected optical beam 110 is collected and sent to the detector 114 (e.g., spectrometer 114). And, by observing the spectral location of the resonant wavelength (peak), one can monitor binding or refractive index changes on or near the biosensor's surface 126. The spectral interrogation concept is graphically represented in the graph shown in FIG. 4. In the present invention, the focus in the description is on the method of spectral interrogation even though the present invention can be partly used for either interrogation method. In addition, the present invention can focus on an instrument configuration 100 where one sends a wide spectrum to the biosensor 102 and measures the wavelength that is reflected by the biosensor 102. And, the same concepts of the present invention can also be used in an instrument configuration 100 that uses a tunable wavelength source 104 and measures the power reflected by the biosensor 102 as a function of the wavelength of the tunable wavelength source 104.

Filtering Interference Fringes

Figure 5:
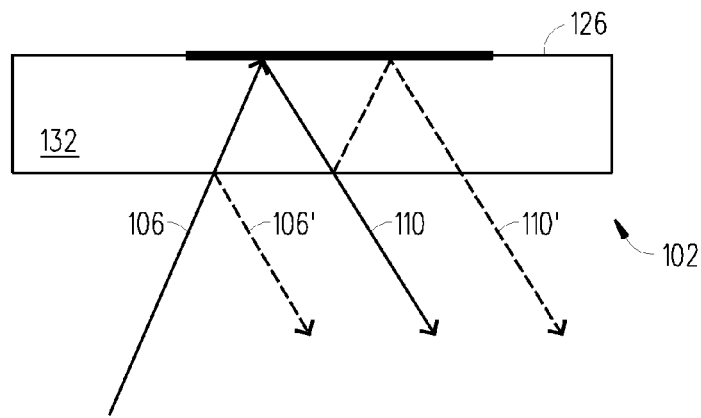
Figure 6:
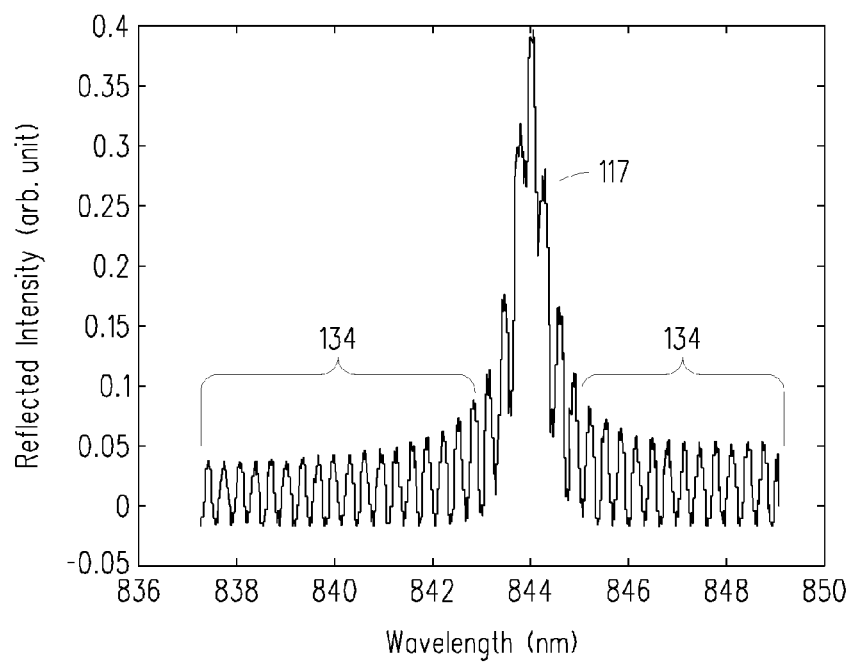

One problem commonly associated with interrogating the biosensor 102 is caused when a part of the optical beam 106 is reflected on the first face of the biosensor's substrate 132 before the optical beam 106 is reflected by the biosensor's top surface 126. Once the optical beam 106 is reflected by the biosensor's top surface 126, a part of it can also be reflected again by the first face of the biosensor's substrate 132. These parasitic reflections 106' and 110' are shown in FIG. 5. The presence of parasitic reflections 106' and 110' cause the generation of fringes 134 in the received optical beam 106', 110 and 110' that are equivalent to Fabry-Perot cavity fringes. FIG. 6 is a graph that illustrates the spectrum of a spectral resonance 117 which has these fringes 134. This graph was generated by a high resolution spectrometer 114 which had a resolution that was much smaller than the period of the fringes 134.

A known solution that can be used to reduce the problem associated with the fringes 134 caused by the parasitic reflection 106' includes inserting an optical isolator 136 between the lensed fibers 108 and 112 and the biosensor's substrate 132 (see FIG. 1). This solution is described in the co-assigned U.S. Patent Application No. US20050264818 A1 entitled "Optical Interrogation Systems with Reduced Parasitic Reflections and a Method for Filtering Parasitic Reflections". The contents of this document are incorporated by reference herein.

Figure 7:
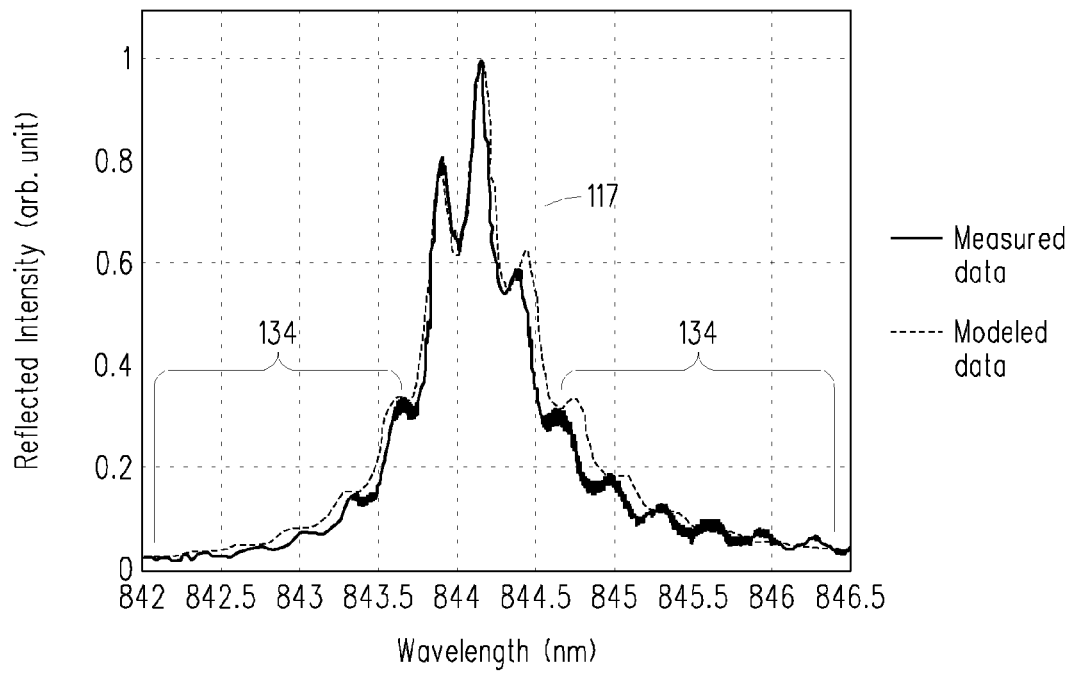

The optical isolator 136 works well to filter out the parasitic reflection 106' which is reflected from the first face of the substrate 132. However, the optical isolator 136 can not filter the parasitic reflection 110' created within the biosensor 102. Because, once the optical beam 110 has been reflected within the biosensor 102, it becomes linearly polarized. As a result, the optical isolator 136 can not filter the parasitic reflection 110'. As shown in FIG. 7, the use of the optical isolator 136 significantly attenuates the fringes 134 in the tails of the spectral resonance 117 but some residual modulation can still be observed (compare to FIG. 6 in which an optical isolator 136 was not used).

Figure 8:
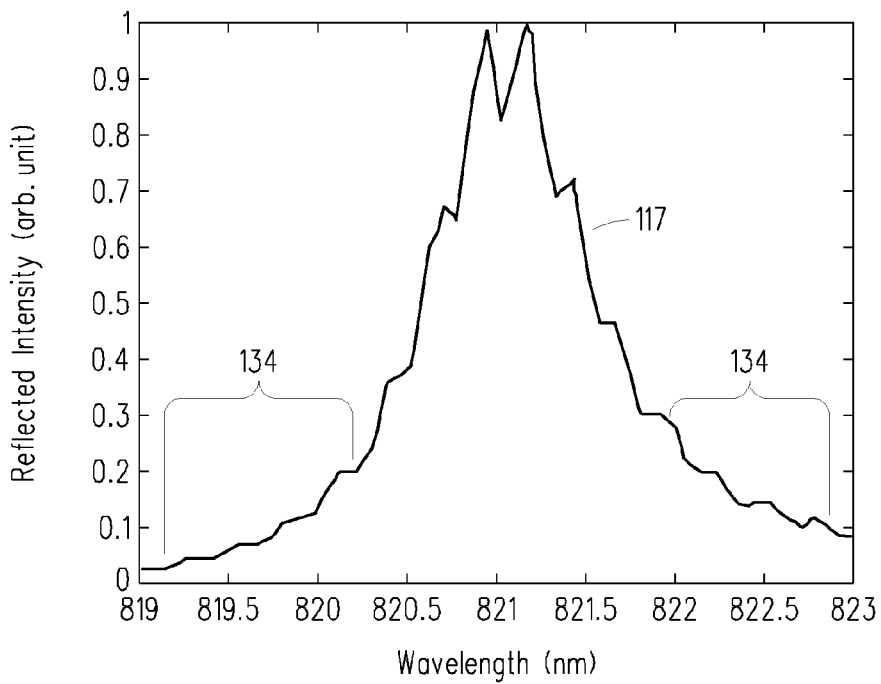

The visibility of the fringes 134 is a function of four main factors. The first factor is the spectrometer's resolution. The second factor is the signal sampling which depends on the spectrometer's pixel size and dispersion. The third factor is the width of the spectral resonance 117. And, the fourth factor is the fringe period which depends on the thickness and index of refraction of the biosensor's substrate 132. For example, FIG. 8 is a graph that shows a spectral resonance 117 that was experimentally obtained by a medium resolution spectrometer 114 (one whose resolution is comparable to the fringe period). In this example, the optical resonance's width was approximately 0.9 nm, the spectrometer's resolution was 0.18 nm and the sampling was 0.09 nm. The fringe period was on the order of 0.33 nm.

The present invention removes/reduces the impact of these fringes 134 on the resonance position determination by applying a low pass filter 138 to the measured signal 116/spectral resonance 117. There are several different types of low pass filters 138 that can be used. For instance, one can calculate the convolution product between the measured signal 116 and another function that can be a rectangular function or a Gaussian function (for example). This exemplary low pass filter 138 is represented as follows:

$$Y' = G \otimes y$$

Where
y is the signal
$\otimes$ represents a convolution product
G is the filter function (e.g., Gaussian, rectangle (boxcar function), sinc, ...)
Y' is the filtered signal 120

In another example, one can calculate the Fourier transform of the measured signal 116 and then multiply this Fourier transform by a filter function. The filtered signal 120 is then obtained as the inverse Fourier transform of this product. This exemplary low pass filter 138 is represented as follows:

$$Y1 = G * FFT(y)$$

$$Y' = FFT^{-1}(Y1)$$

Where
y is the signal
G is the filter function
FFT is the Fourier transform
$FFT^{-1}$ is the inverse Fourier transform
Y' is the filtered signal 120

Another solution to this problem can also consist of intentionally decreasing the resolution of the spectrometer 114. One way to do this with a conventional grating based spectrometer 114, involves misaligning the focus of the entrance spectrometer slit or fiber. Although this solution works, it is not the preferred approach because of the fact that measurement noise is proportional to the square root of the resonance width. Thus, when the spectrometer 114 is misaligned, the width of the spectral resonance 117 increases which in turn increases the uncertainty in the estimate of the location of the spectral resonance 117.

Figure 9:
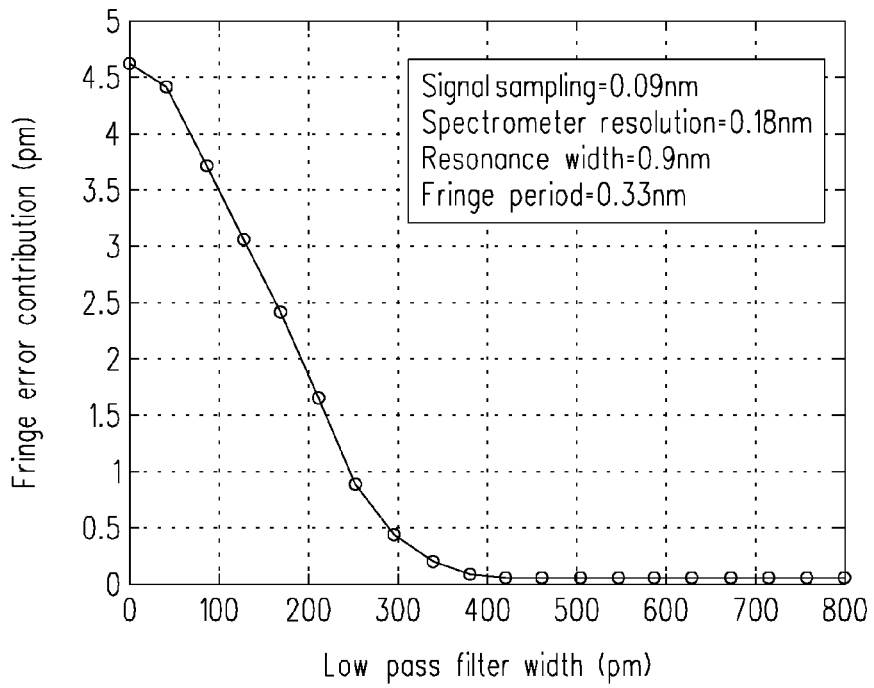

To validate the advantages of using the low pass filter algorithm 138, a typical spectral resonance 117 including parasitic reflection fringes 134 was calculated. Then, the maximum deviation (or fringe error contribution) of the resonance location, estimated by a centroid algorithm, from the true resonance location was calculated. The fringe error contribution was generated in an estimate of the optical resonance's location as fringes 114 were moved across the resonance peak by changing their phase (or location relative to the resonance peak). For example, a centroid calculation was performed to estimate the location of the optical resonance. FIG. 9 is a graph that shows the evolution of this fringe error contribution as a function of the width of the low pass filter 138 that was applied.

Ideally, one should use a low pass filter 138 with a width which is wide enough to suppress the detrimental effects of the parasitic fringes 134. In theory, there is no upper limit to the width of the low pass filter 138. Indeed, by increasing the low pass filter's width, the resonance is broadened and the measurement noise is filtered. So, although the resonance gets wider because of the low pass filter 138, the noise on the resonance position is not affected. In practice, FIG. 9 shows that there is a limit on the width of the low pass filter 138 which occurs when the fringe error contribution does not change anymore after increasing the width. In the example shown in FIG. 9, the best compromise entails using a low pass filter 138 with a width of around 500 pm.

To implement this embodiment of the present invention, it should be noted that the biosensor 102 combined with the optical interrogation system 100 should satisfy two conditions:

1. The width of the spectral resonance 117 should be significantly larger than the period of the fringes 134. This is equivalent to stating that, when calculating the Fourier transform of the signal, the central lobe associated with the useful part of the signal must be well separated from any side lobes associated with the fringes of higher frequency modulation.
2. The reflected signal 110 should be sampled at a period significantly lower than the period of the fringes 134. If this condition is not fulfilled, then the fringes 134 will generate apparent low frequency deformations of the spectral resonance 117. This undesirable effect is also known as aliasing.

Figure 10:
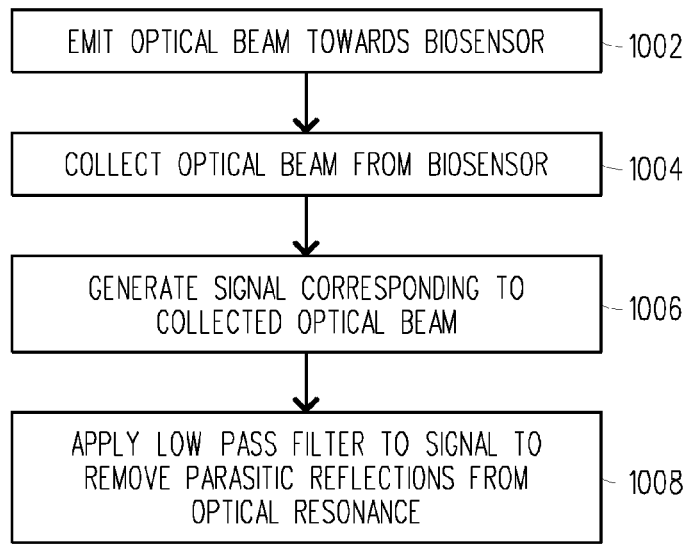

FIG. 10 is a flowchart illustrating the steps of a method 1000 for using the optical interrogation system 100 to interrogate a biosensor 102 and at the same time reduce the measurement noise caused by problematical parasitic reflections 134 in accordance with the first embodiment of the present invention. Beginning at step 1002, the optical interrogation system 100 and in particular a launch system 101 emits an optical beam 106 towards the biosensor 102. At step 1004, the optical interrogation system 100 and in particular a receive system 103 collects an optical beam 110 from the biosensor 102. At step 1006, the optical interrogation system 100 and in particular a spectrometer 114 generates a signal 116 which corresponds to the collected optical 110. Then at step 1008, the optical interrogation system 100 and in particular a processor 118 applies a low pass filter 138 to the signal 116 to digitally remove/reduce the problematic parasitic reflections 134 that are located on each side of a spectral resonance 117.

Spectrometer Pixelation

A second problem that the present invention addresses is caused by the finite size of the CCD pixels in the spectrometer 114. As shown in FIG. 1, light 110 enters the spectrometer 114 and is dispersed and sent to a CCD (charge-coupled device) array 140. Each pixel in the CCD array 140 is mapped to a specific spectral region. This enables the processor 118 to obtain and record a spectrum that shows light intensity as a function of wavelength (or a function of the pixel in the spectrometer 114) when the CCD array 140 is read-out. The optical information that is recorded is "pixelated" that is, it is sampled in finite bins each with a width equal to the width of the respective CCD pixels in the spectrometer 114.

Figure 11:
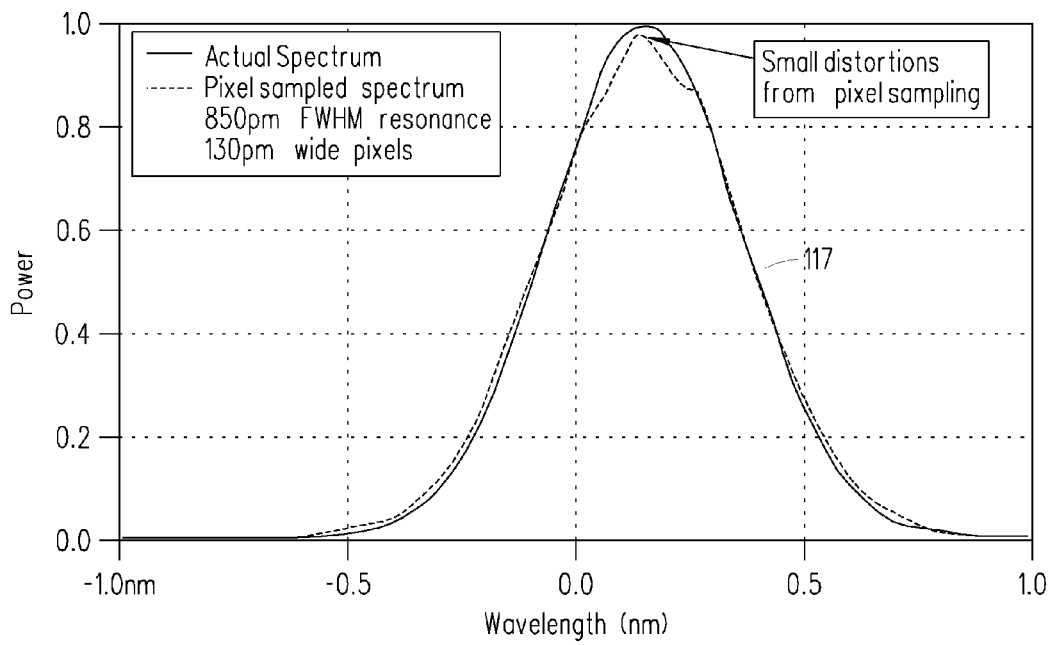
FIGS. 11-24 are drawings and graphs used to help describe how the optical interrogation system can function to reduce measurement artifacts caused by problematical pixelation effects in accordance with the second embodiment of the present invention.

Because each CCD pixel effectively integrates all of spectral energy that falls within it, this can distort the apparent shape of the spectral resonance 117. An example of such a distortion from such a pixelated, or sampled, spectrum is shown in FIG. 11. The amount of distortion depends on the locations of the edges of the CCD pixels relative to the peak of the spectral resonance 117. As such, when the spectral resonance 117 moves across the CCD pixels, this causes a periodic error function in the estimate of location of the spectral resonance 117. This periodic error function or "pixelation oscillation" has a period equal to the size of the CCD pixel. And, the amplitude of the periodic error function depends on the optical resonance width, the CCD pixel size, and the particular algorithm that is chosen to calculate the location of the spectral resonance 117. This pixelation problem is not unique to the spectral method of detection, indeed, it can occur for any sampled spectrum. As such, this problem appears as well in an angular interrogation system that uses a CCD array to spatially sample the reflected angular intensity.

Figure 12:
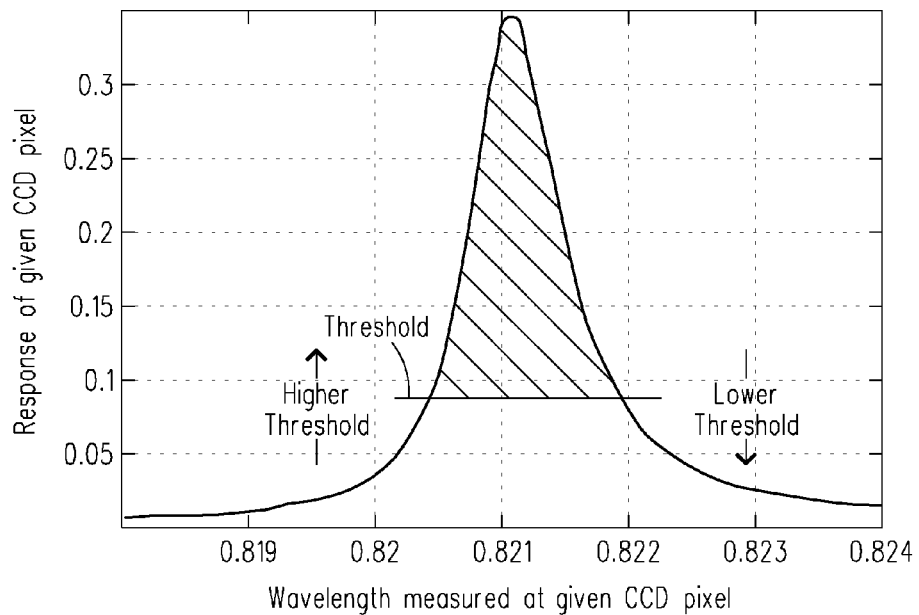

To calculate a periodic error caused by the limited CCD pixel size, a theoretical spectral resonance 117 was simulated and integrated over each CCD pixel. Then, a centroid of the spectral resonance 117 was calculated which has a threshold by applying the following algorithm for all of the points that are above the threshold value:

For all Y>threshold:

$Y' = Y - \text{threshold}$ $\text{Centroid} = (\Sigma X^* Y')/(\Sigma Y')$ where Y is the response of a given CCD pixel, and X is the wavelength measured at a given CCD pixel. The purpose of the threshold is to exclude background that is not part of the spectral resonance 117. This concept of a threshold for the algorithm is graphically illustrated in FIG. 12.

Figure 13:
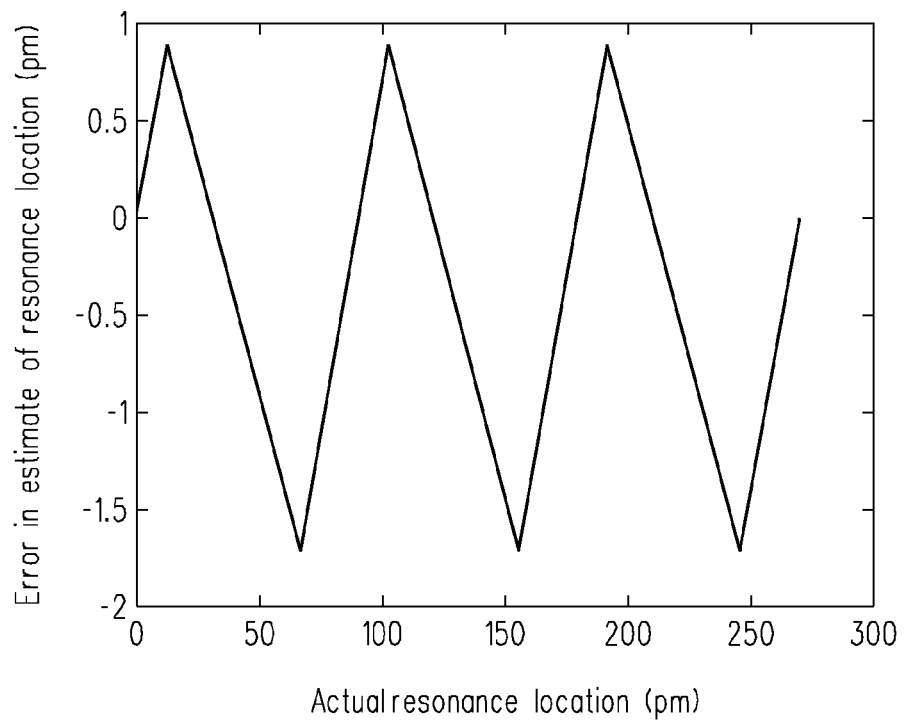

The centroid that is calculated by this algorithm is a function of the location of the spectral resonance 117 on the CCD array. FIG. 13 is a graph that shows a periodic error function which is the deviation between the actual location of the spectral resonance 117 and the algorithm's estimate of the optical resonance's location. This periodic error function was obtained by assuming a 0.85 nm resonance width and a 0.09 nm pixel size. In addition, the spectral resonance 117 was assumed to move 0.27 nm and the threshold was set at 25% of the maximum power in the optical resonance's peak.

Figure 14:
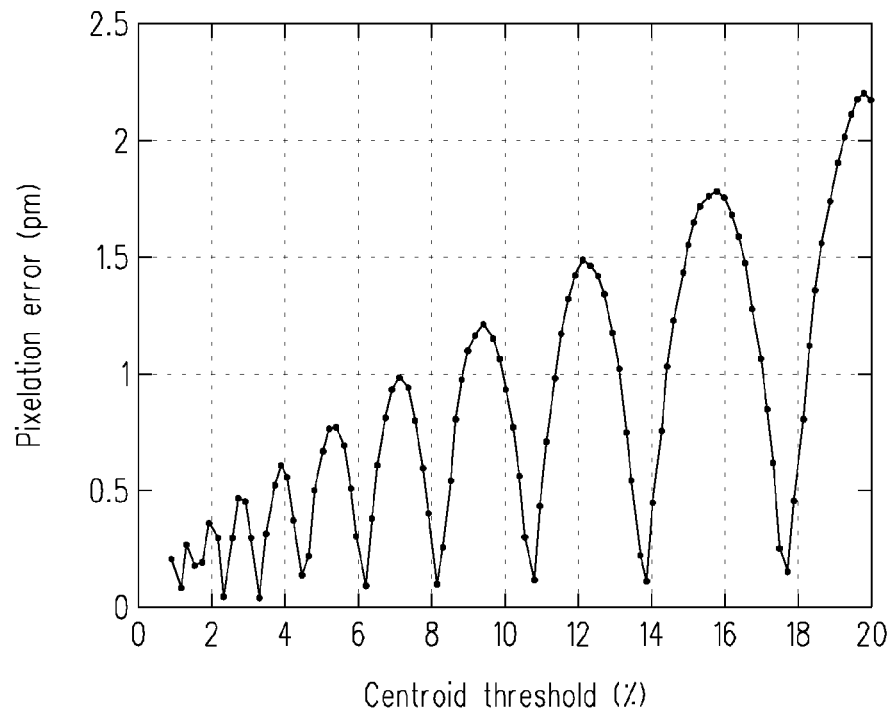

One approach that can be used to minimize the pixelation error involves decreasing (lowering) the threshold level. FIG. 14 is a graph that shows a pixelation error that was calculated as a function of the threshold level. As can be seen, the further the threshold is lowered, the greater the amount of signal energy that will be included in the calculation of the resonance location, and the more accurate the location estimate becomes. In contrast, the higher the threshold means that less signal energy will be included in the calculation of the resonance location, and the less accurate the location estimate becomes.

However, a problem with decreasing the threshold level is that the wavelength window over which the centroid is calculated is made considerable larger. This means that the centroid calculation includes not just more energy from the spectral resonance 117, but it also includes energy from noise sources (e.g., detector dark current) which are always present in a practical optical interrogation system. Moreover, as the threshold line is dropped further and further, only small incremental amounts of additional signal energy are added, since the resonance amplitude drops off, but a lot of noise energy is added, since the noise typically scales with the bandwidth used in the calculation (i.e. the number of CCD pixels or wavelength range included). As such, the dropping of the threshold line all the way to zero to avoid pixelation induced error would considerably increase the noise content and impair the estimate of the optical resonance location.

Figure 15:
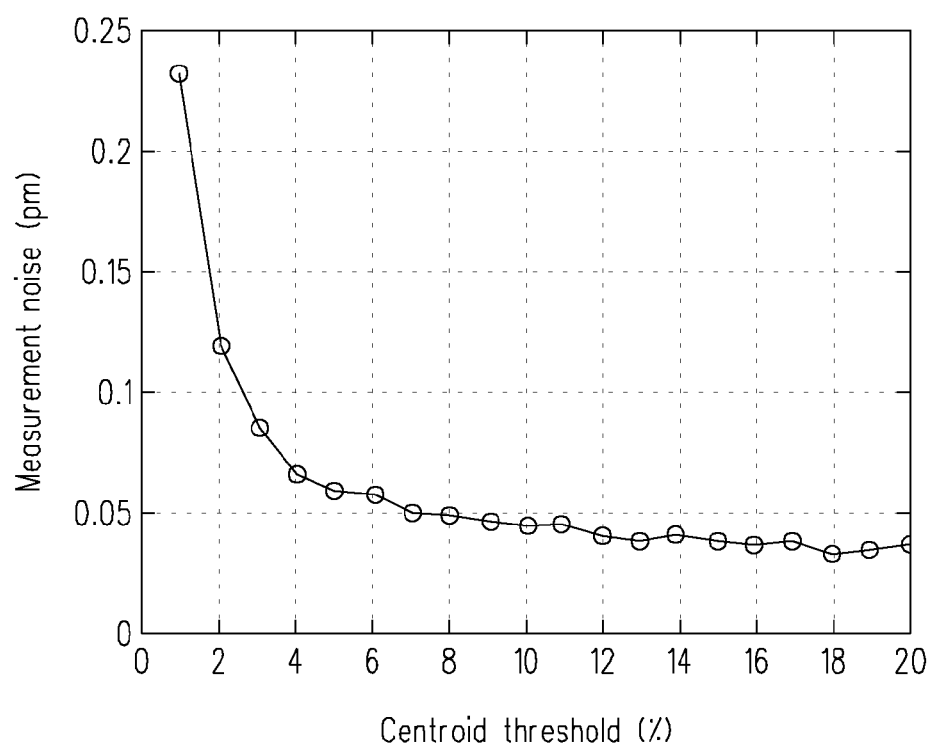
Figure 16:
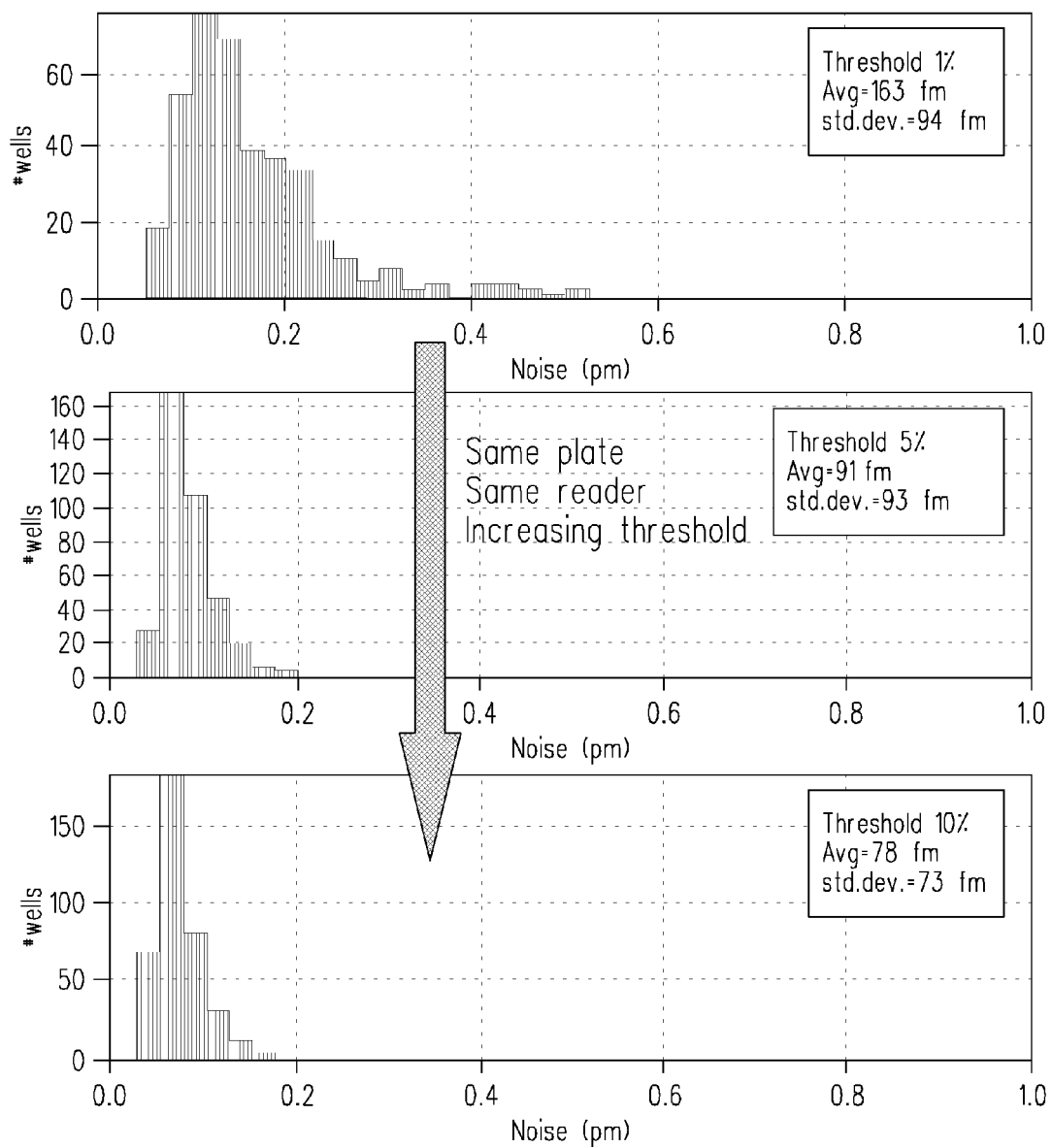

To help illustrate the impact of the threshold on the measurement noise, FIG. 15 is provided which shows a theoretical model of the impact of lowering the threshold on the measurement noise. And, the impact of raising the threshold level in an experiment with a centroid calculation is shown in the graphs of FIG. 16. In this experiment, a 10 minute measurement of 384 resonant waveguide grating sensors 102 placed in a micro well plate, and soaked with water, was used to evaluate the system's noise. It can be clearly seen that the raising of the threshold enhances the system's performance. However, as the threshold is increased, the pixelation induced error becomes a problem.

Alternative algorithms besides the centroid algorithm have been used in the past to help remove this pixelation induced error. Examples of these alternative algorithms include, but are not limited to: (1) peak fitting to a known resonance shape; (2) using a knife edge function; and (3) using a correlation function with a known resonance shape. Some of these algorithms seek to remove the pixelation of the data by essentially "undoing" the integration of the signal energy that was performed by the CCD pixels. However, all of these algorithms still suffer from the same problem that is associated with the centroid algorithm. Again, if an algorithm does not use any threshold, then the tails 134 of the spectral resonance 117 are involved in the calculation and the measurement noise increases. And, if an algorithm uses a threshold, then the same periodic error function is observed as was in the centroid algorithm.

Figure 17:
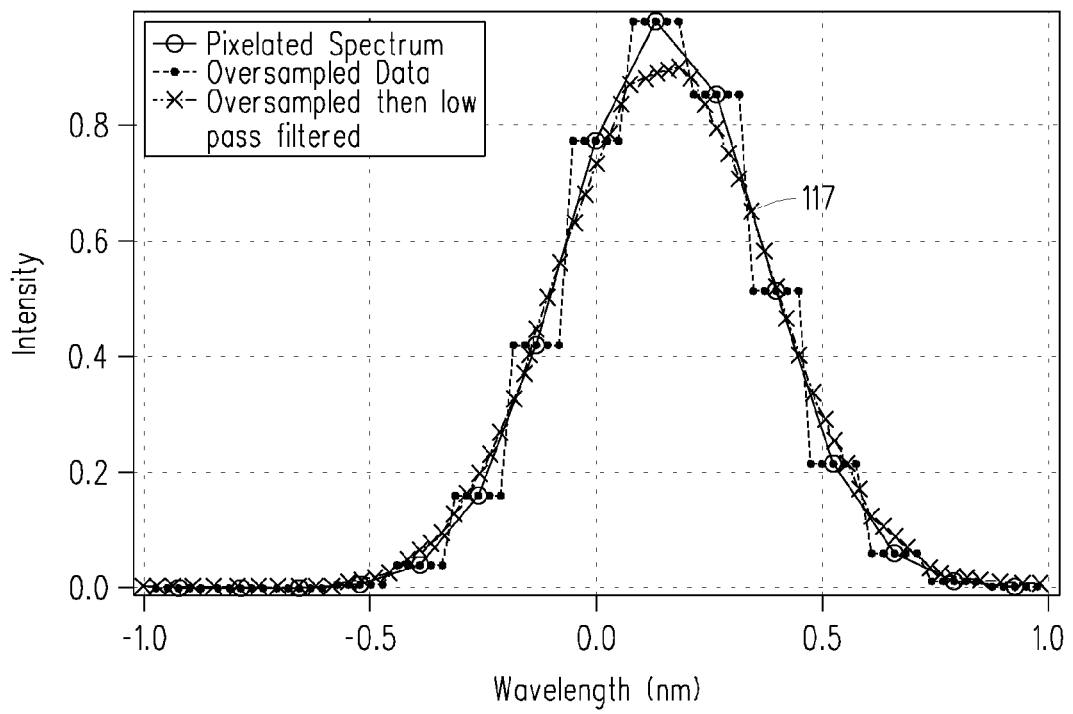

The present invention addresses this problem by numerically "oversampling" the spectral resonance 117 and then calculating a centroid over the "oversampled" signal. The oversampling entails replicating each data point into N data points with a signal or intensity value identical to the original point, but positioned in wavelength (or pixel number) at steps of $\Delta\lambda/N$, rather than the original data spacing of $\Delta\lambda$. In this way, the data array is expanded by a factor N. A graphic illustration of such an oversampling process 142 is shown in FIG. 17.

Once, the data is oversampled then a low pass filter (like the one described in the first embodiment), interpolation, or some other smoothing operation is applied. The centroid is then calculated on the smoothed signal. Alternatively, the smoothing operation can be performed in the oversampling process. And, now when the spectral resonance 117 moves across the CCD pixels the errors caused by the pixelation induced oscillation are reduced or eliminated. Also of note is that this elimination of the pixelation induced oscillation can be accomplished if the oversampling and filtering are performed on the entire spectral resonance 117 or if they are performed only close to the area were the threshold in the centroid crosses the resonance curve (see FIG. 12).

It should be appreciated that this technique is not the only technique that may be used to reduce the impact of pixelation. Some exemplary algorithms that can be used for signal oversampling (and possible filtering) in accordance with the present invention are as follows:

Exemplary Algorithm 1: Oversampling using a cubic spline interpolation:

The cubic spline effects both an oversampling and a smoothing since an interpolation is implicit in the cubic spline technique. Therefore, no additional low pass filter is necessary.

Exemplary Algorithm 2: Fourier method:

Calculate the Fourier transform of the spectral resonance 117.

Multiply by a low pass filter function to filter the fringes 134 and eliminate the power at high frequencies.

Add zero's on the left and right of the filtered function.

Calculate the inverse Fourier transform to obtain the filtered/oversampled optical resonance 120.

Exemplary Algorithm 3: Step function:

Oversample the spectral resonance 117 to make it look like a stairstep function.

Convolve the oversampled optical resonance by a filter function such as a Gaussian function. This simultaneously filters the fringes 134 and smoothes the steps of the oversampled optical resonance.

Figure 18:
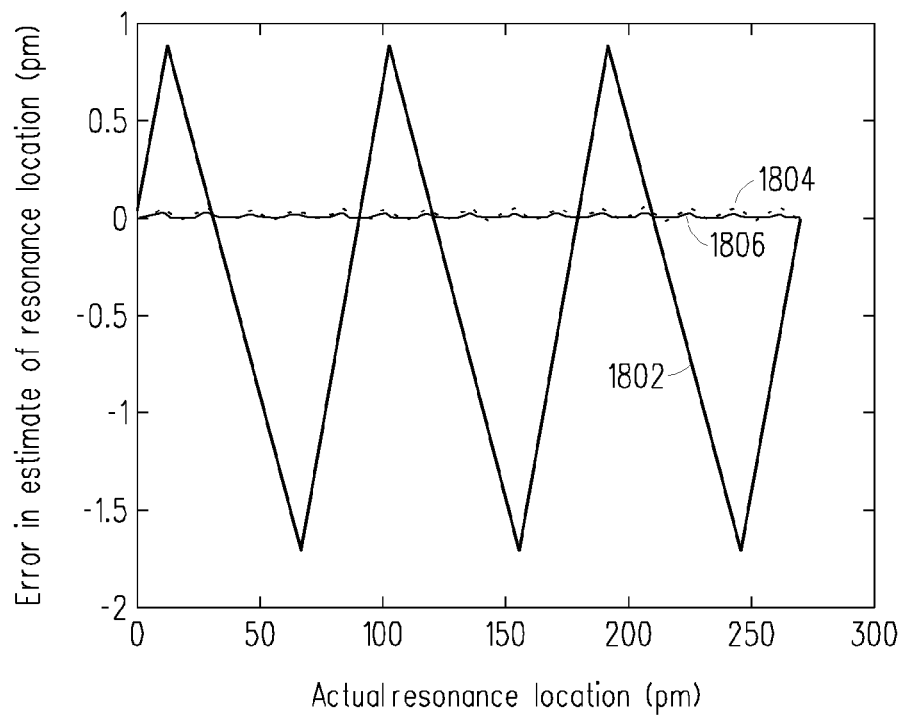

FIG. 18 is a graph that shows a calculation of the periodic error function that was made with and without oversampling. The function 1802 that shows a variation of approximately 2.5 pm was calculated with only a centroid algorithm (see also FIG. 13). And, the two other functions 1804 (# oversamples per pixel=5) and 1806 (# oversamples per pixel=6) where calculated with the oversampling process 142 in accordance with the present invention.

To validate the oversampling process, an experiment was conducted with a LID microplate. In the experiment, hot water was placed into one of the sensor wells to generate a spectral resonance 117 whose spectral position varied over time. Then, by using a fiber optic beam splitter, the reflected light was split and sent into 8 different spectrometers (this setup is not shown). If the detected spectral resonance 117 is free of measurement errors such as fringes 134 and pixelation, then the 8 centroids should perfectly track each other within any constant offset of each spectrometer.

Figure 19:
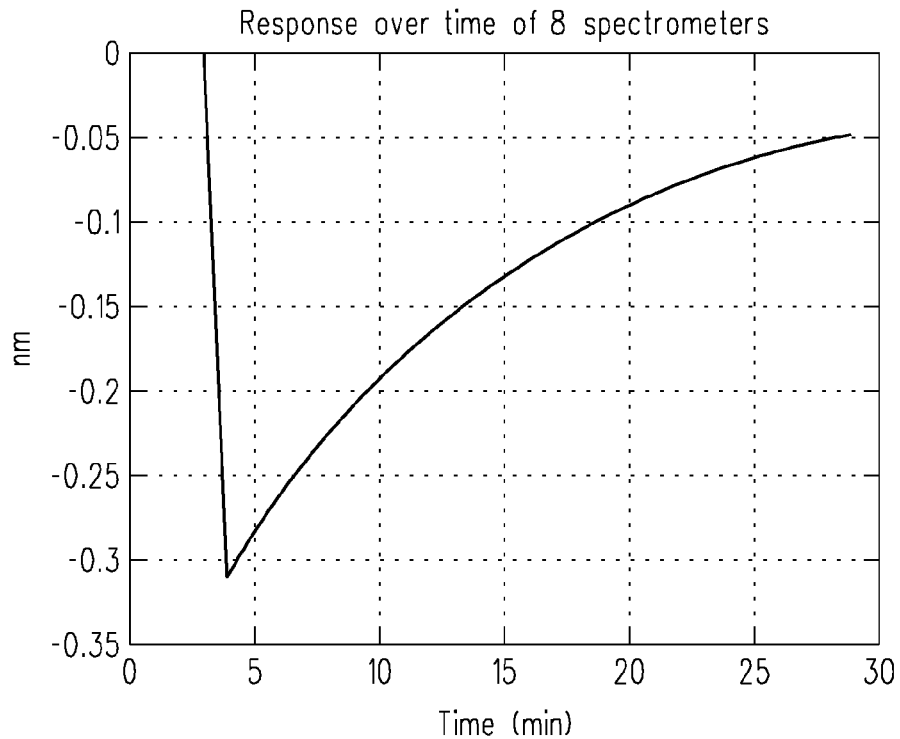

FIG. 19 is a graph that shows the evolution of the centroid observed by the 8 spectrometers that was calculated when the centroid algorithm was directly applied without filtering or oversampling. In this case, a constant offset (calibration) was removed from each spectrometer, by assigning the first measurement of each spectrometer to a value of zero wavelength shift. As a result, the subsequent measurements were all measured as a shift relative to the starting wavelength. As can be seen, there is an initial downward spike when the hot water was added, and then a slow exponential rise in wavelength as the water above the sensor cooled. It can also be seen that all 8 spectrometers observed a very similar wavelength shift. Indeed, based on the scale shown in FIG. 19 it can be seen that all 8 traces are "almost" completely overlaid on top of one another.

At first glance this appears to be good, but when an optical detection system 100 interrogates a RWG sensor 102 (resonance waveguide grating sensor 102) then even a very small wavelength measurement discrepancy can be significant to the end user. For instance, if a small biochemical binding signal may ride upon a large change in a bulk refractive index change. Then, to reference out the bulk refractive index change, one spectrometer may be used observe a sensor 102 in a well with the biochemical binding plus the bulk refractive index shift. And, another spectrometer may be used to observe a sensor 102 in a control well with no biochemical binding but with the same bulk refraction index solution added. If both spectrometers report the exact same bulk refractive index change, then the bulk index shift may be referenced out by subtracting the two signals, leaving only the biochemical biding shift of interest. Unfortunately, the bulk refractive index change could be as large as 100 pm ($10^{-3}$ RIU), while the binding signal could be as small as 1 pm ($10^{-5}$ RIU). In that case, both spectrometers must report the same bulk refractive index change to an accuracy of <<1 pm (<<1% of the bulk index shift), otherwise the small 1 pm binding signal will be overwhelmed by measurement uncertainty. Therefore, ensuring the linearity of the spectrometer or algorithm response to levels of ~100 fm is important.

Figure 20:
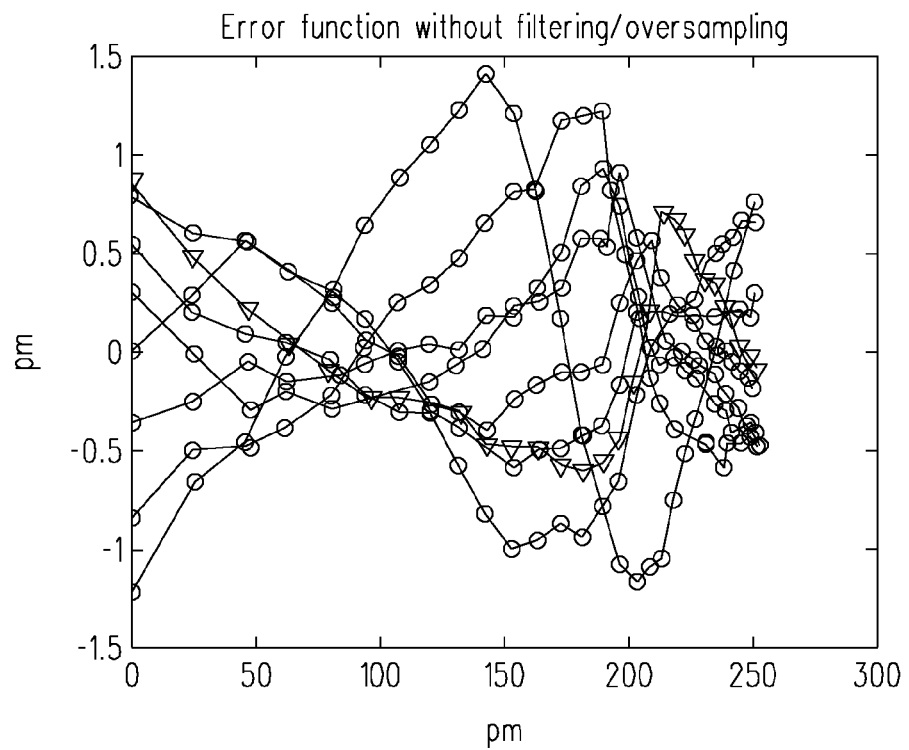

To visualize the peak location errors of each spectrometer on such a fine scale, one can calculate the difference (or residual) between the peak location calculated by each spectrometer and the mean value of the peak location calculated by all 8 spectrometers. FIG. 20 is a graph that shows such a residual error function. Here spectrometer to spectrometer discrepancies can be observed that are on the order of 3 pm peak to valley, which is well above the desired linearity requirement of an optical interrogation system 100. This problem is addressed by the present invention.

Figure 21:
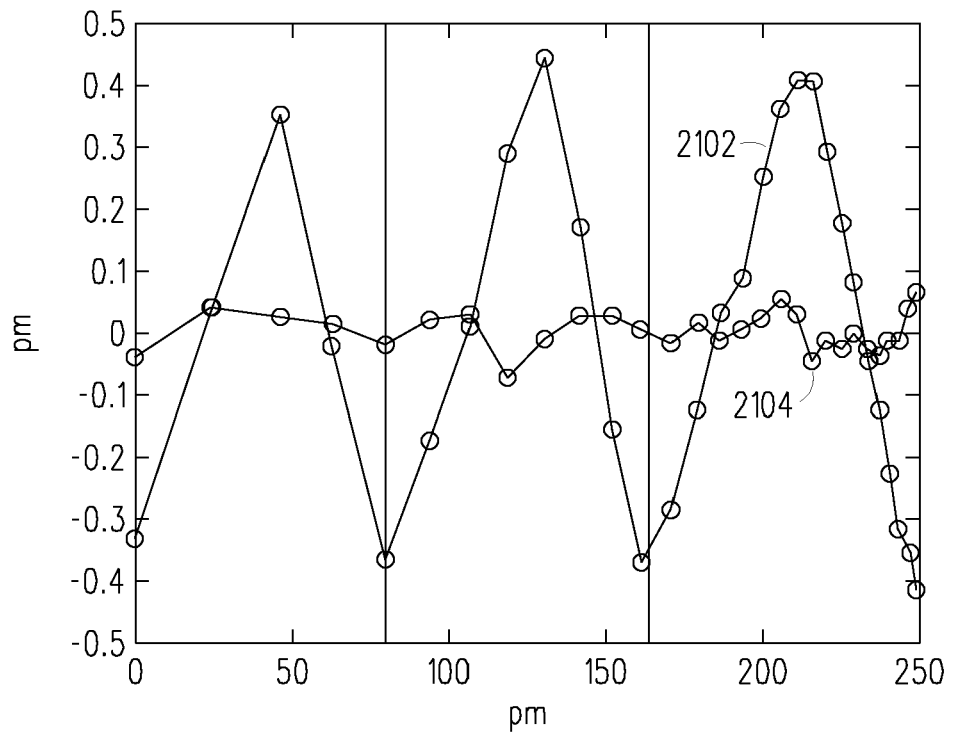
Figure 22:
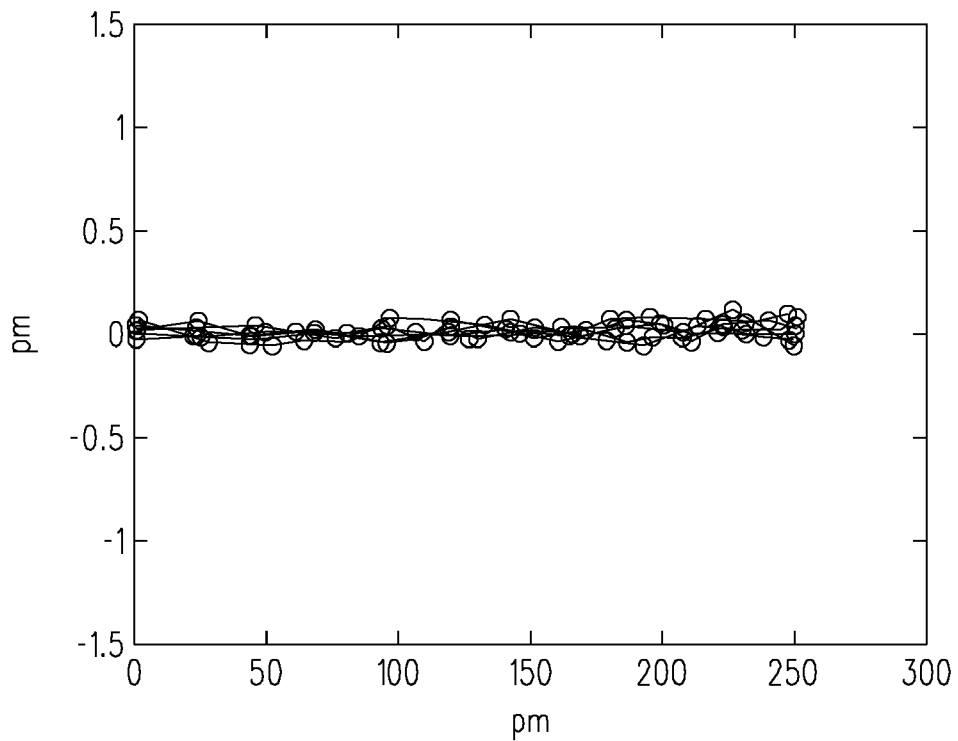

If a low pass filter (without oversampling) was applied to the same set of data, then a residual error function 2102 would be obtained like the one shown in the graph of FIG. 21. As can be seen, the amplitude of the periodic error is reduced, but a periodic error still remains, with a period close to 0.09 nm which corresponds to the size of the spectrometer's pixel. This periodic error remains because of the pixelation of the spectra, and the fact that a 25% threshold level was used. However, if one oversamples the data by N=5 and then applies a low pass filter of width 500 pm then they would obtain a residual error function 2104 that is shown in FIG. 21. In this case, the amplitude of the residual error function 2104 is dramatically reduced to levels below 50 fm. To illustrate this point, FIG. 22 was prepared which shows the residual error functions of all 8 spectrometers after a oversampling/low pass filter algorithm was applied on the same scale that was used to prepare the graph in FIG. 20. As can be seen, there is a marked improvement when the oversampling/low pass filter algorithm of the present invention is used. In this example, the noise was reduced to 0.03 pm at one standard deviation.

Figure 23:
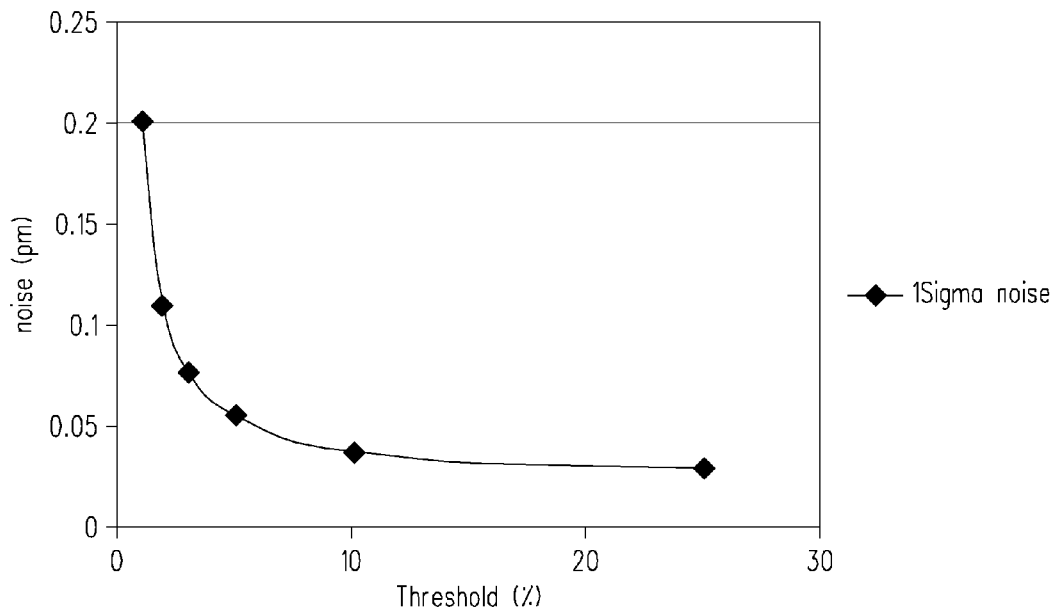

To help illustrate the impact that different threshold levels can have on the measurement noise when the oversampling/low pass filter algorithm is used, reference is made to FIG. 23. FIG. 23 is a graph that illustrates how the noise can be reduced when the threshold level is increased. It is only by using the oversampling based algorithm that one can increase the threshold level to 10% and above without suffering from the penalty of pixelation induced non-linearity. Therefore, such an algorithm is not only important for reducing non-linearities, but it is also important for allowing one to increase the threshold and it is important for obtaining the optimum noise performance from the optical interrogation system 100.

Figure 24:
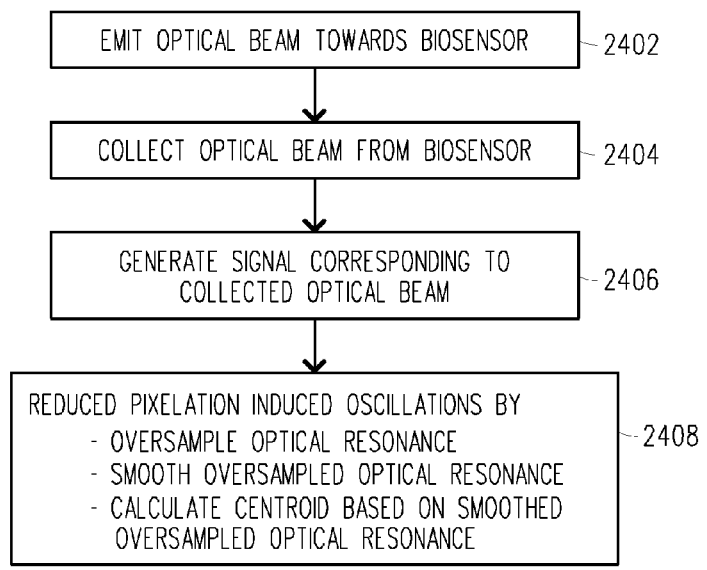

FIG. 24 is a flowchart illustrating the steps of a method 2400 for using the optical interrogation system 100 to interrogate a biosensor 102 and at the same time reduce the measurement artifacts caused by the problematical pixelation effect in accordance with the second embodiment of the present invention. Beginning at step 2402, the optical interrogation system 100 and in particular a launch system 101 emits an optical beam 106 towards the biosensor 102. At step 2404, the optical interrogation system 100 and in particular a receive system 103 collects an optical beam 110 from the biosensor 102. At step 2406, the optical interrogation system 100 and in particular a spectrometer 114 generates a signal 116 which corresponds to the collected optical 110. Then at step 2408, the optical interrogation system 100 and in particular a processor 118 reduces pixelation oscillations in the signal 116 by: (a) oversampling at least a portion of the spectral resonance 117; (b) smoothing the spectral resonance 117; and (c) calculating a resonance location or centroid that is based on the smoothed-oversampled spectral resonance 117. The resonance location or centroid can be calculated by using any peak locating routine (e.g., peak fitting to a known resonance shape, correlation function, or a weighted (or higher order) centroid knife edge). It should be appreciated that the oversampling step and the smoothing step are interchangeable.

From the foregoing, it should be appreciated by those skilled in the art that the present invention relates to an algorithm for peak detection that can be applied to LID sensors and, more specifically, to a method for filtering parasitic fringes and minimizing the detection error that is generated by the finite pixel size of the detector. This algorithm has been applied to a broadband spectral interrogation LID instrument where both parasitic fringe filtering and sensor pixel size matter. However, this algorithm could also be applied to other instrument architectures that: (1) interrogate a resonant waveguide gratings with a tunable laser; (2) interrogate a resonant waveguide grating sensor with an angular technique; and (3) interrogate a surface plasmon resonance sensor with either a spectral or angular technique.

For a more detailed discussion about the structure of a preferred biosensor 102 described herein, reference is made to the following documents:

U.S. Pat. No. 4,815,843 entitled "Optical Sensor for Selective Detection of Substances and/or for the Detection of Refractive Index Changes in Gaseous, Liquid, Solid and Porous Samples".

K. Tiefenthaler et al. "Integrated Optical Switches and Gas Sensors" Opt. Lett. 10, No. 4, April 1984, pp. 137-139.

The contents of these documents are incorporated by reference herein.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. An optical interrogation system comprising:
a launch system that emits an optical beam towards a biosensor;
a receive system that collects an optical beam from the biosensor and then outputs a signal which corresponds to the collected optical beam;
a processor that applies a low pass filter to the signal to digitally remove a plurality of problematic parasitic reflections located within the signal that represents an optical resonance; and
an optical isolator located between the biosensor and both a lensed fiber of the launch system and a lensed fiber of the receive system, wherein the optical isolator filters out the parasitic reflections caused by a part of the optical beam reflected from a face of a substrate of the biosensor, and wherein the optical isolator does not filter out the parasitic reflections caused by the optical beam which passes through the substrate and is reflected from a top surface of the biosensor.

2. The optical interrogation system of claim 1, wherein said low pass filter is represented as follows:

$$Y' = G \otimes y$$

where:
y is the signal;
$\otimes$ represents a convolution product;
G is a filter function; and
Y' is a filtered signal.

3. The optical interrogation system of claim 2, wherein the filter function is:
a Gaussian function;
a rectangular function; or
a sinc function.

4. The optical interrogation system of claim 1, wherein said low pass filter is represented as follows:

$$Y1 = G * FFT(y); \text{ and}$$

$$Y' = FFT^{-1}(Y1)$$

where:
y is the signal;
G is a filter function;
FFT is a Fourier transform;
$FFT^{-1}$ is an inverse Fourier transform; and
Y' is a filtered signal.

5. The optical interrogation system of claim 4, wherein the filter function is:
a Gaussian function;
a rectangular function; or
a sinc function.

6. The optical interrogation system of claim 1, wherein the receive system includes a spectrometer which has a misaligned entrance spectrometer slit or fiber.

7. The optical interrogation system of claim 1, wherein the low pass filter has a width sized to suppress detrimental effects of the parasitic reflections.

8. The optical interrogation system of claim 1, wherein the optical resonance includes a spectral resonance with a width that is larger than a period of parasitic fringes.

9. The optical interrogation system of claim 1, wherein the receive system samples the optical beam collected from the biosensor at a period lower than a period of parasitic fringes which are on each side of the optical resonance.

10. The optical interrogation system of claim 1, wherein the low pass filter filters out the parasitic reflections caused by the optical beam which passes through the substrate of the biosensor and is then reflected from the top surface of the biosensor.

11. An optical interrogation system comprising:
a launch system that emits an optical beam towards a biosensor;
a receive system that collects an optical beam from the biosensor and then outputs a signal which corresponds to the collected optical beam; and
a processor that applies a low pass filter to the signal to digitally remove a plurality of problematic parasitic reflections located within the signal that represents an optical resonance, wherein the low pass filter filters out the parasitic reflections caused by the optical beam which passes through a substrate of the biosensor and is then reflected from a top surface of the biosensor, and wherein the low pass filter does not filter out the parasitic reflections caused by a part of the optical beam reflected from a face of the substrate of the biosensor.

12. The optical interrogation system of claim 11, further comprising an optical isolator located between the biosensor and both a lensed fiber of the launch system and a lensed fiber of the receive system, wherein the optical isolator filters out the parasitic reflections caused by a part of the optical beam reflected from the face of the substrate of the biosensor, and wherein the optical isolator does not filter out the parasitic reflections caused by the optical beam which passes through the substrate and is reflected from the top surface of the biosensor.

13. A method for interrogating a biosensor, said method comprising the steps of:
emitting an optical beam towards the biosensor;
collecting an optical beam from the biosensor;
generating a signal which corresponds to the collected optical beam;
applying a low pass filter to the signal to digitally remove a plurality of problematic parasitic reflections located within the signal that represents an optical resonance; and
using an optical isolator to filter out the parasitic reflections caused by a part of the optical beam reflected from a face of a substrate of the biosensor while the optical isolator does not filter out the parasitic reflections caused by the optical beam which passes through the substrate and is reflected from a top surface of the biosensor.

14. The method of claim 13, wherein said low pass filter is represented as follows:

$$Y' = G \otimes y$$

where:
y is the signal;
$\otimes$ represents a convolution product;
G is a filter function; and
Y' is a filtered signal.

15. The method of claim 14, wherein the filter function is:
a Gaussian function;
a rectangular function; or
a sinc function.

16. The method of claim 13, wherein said low pass filter is represented as follows:

$$Y1 = G * FFT(y); \text{ and}$$

$$Y' = FFT^{-1}(Y1)$$

where:
y is the signal;
G is a filter function;
FFT is a Fourier transform;
$FFT^{-1}$ is an inverse Fourier transform; and
Y' is a filtered signal.

17. The method of claim 16, wherein the filter function is:
a Gaussian function;
a rectangular function; or
a sinc function.

18. The method of claim 13, wherein the optical resonance include a spectral resonance with a width that is larger than a period of parasitic fringes.

19. The method of claim 13, wherein the collecting step includes a step of sampling the optical beam collected from the biosensor at a period lower than a period of parasitic fringes which are on each side of the optical resonance.

20. The method of claim 13, wherein the low pass filter filters out the parasitic reflections caused by the optical beam which passes through the substrate of the biosensor and is then reflected from the top surface of the biosensor.

21. A method for interrogating a biosensor, said method comprising the steps of:
emitting an optical beam towards the biosensor;
collecting an optical beam from the biosensor;
generating a signal which corresponds to the collected optical beam; and
applying a low pass filter to the signal to digitally remove a plurality of problematic parasitic reflections located within the signal that represents an optical resonance, wherein the low pass filter filters out the parasitic reflections caused by the optical beam which passes through a substrate of the biosensor and is then reflected from a top surface of the biosensor, and wherein the low pass filter does not filter out the parasitic reflections caused by a part of the optical beam reflected from a face of the substrate of the biosensor.

22. The method of claim 21, further comprising a step of inserting an optical isolator between the biosensor and both a lensed fiber of the launch system and a lensed fiber of the receive system, wherein the optical isolator filters out the parasitic reflections caused by a part of the optical beam reflected from the face of the substrate of the biosensor, and wherein the optical isolator does not filter out the parasitic reflections caused by the optical beam which passes through the substrate and is reflected from the top surface of the biosensor.

* * * * *